United States Patent [19]

Norden-Paul et al.

[11] Patent Number: 5,247,611
[45] Date of Patent: Sep. 21, 1993

[54] SPREADSHEET CELL HAVING MULTIPLE DATA FIELDS

[75] Inventors: Ronald Norden-Paul, Mesa; John Brimm, Scottsdale; Richard Shelton, Mesa, all of Ariz.

[73] Assignee: Emtek Health Care Systems, Inc., Tempe, Ariz.

[21] Appl. No.: 689,135

[22] Filed: Apr. 22, 1991

Related U.S. Application Data

[63] Continuation of Ser. No. 408,166, Sep. 15, 1989, abandoned.

[51] Int. Cl.⁵ ............................................. G06F 15/66
[52] U.S. Cl. .................................. 395/161; 395/155; 345/156
[58] Field of Search ............... 364/518, 521, 522, 523; 390/703, 706, 747, 750; 395/155, 161, 157, 156, 158, 159, 160

[56] References Cited

U.S. PATENT DOCUMENTS 4,811,240  3/1989  Ballou et al. ..................... 364/518
4,811,241  3/1989  Liang ................................. 364/518
4,817,043  3/1989  Brown ............................... 364/518
4,839,806  6/1989  Goldfischer et al. .......... 364/413.02
4,893,256  1/1990  Rutherford et al. .............. 364/518

FOREIGN PATENT DOCUMENTS 0211151  2/1987  European Pat. Off.

OTHER PUBLICATIONS

Butterworth, Forms Definition Methods, 1986 Conference Proceedings p. 708, IEEE Computer Society, Phoenix Conference on Computer and Communications, Mar. 26-28, 1986.

John E. Brimm, MD, "Computers in Critical Care", Critical Care Nursing Quarterly 1987; 9(4):53-63.

"PDMS-Patient Data Management System-System Description" Hewlett Packard (Jan. 1982).

"PDMS-Patient Data Management System-Clinical User's Guide" Hewlett Packard (Jan. 1982).

"Ulticare-A Bedside Patient Care Information System" Health Data Sciences (Oct. 1984).

Primary Examiner—Phu K. Nguyen
Attorney, Agent, or Firm—Harold C. McGurk, IV; Walter W. Nielsen; Raymond Warren 4 Claims, 12 Drawing Sheets

FIG. 2

| | | 102 | | | DOE, JOHN K.<br>H 08/19/40 01-56-16 | 9NB<br>ALLERGIES: CODINE |
|---|---|---|---|---|---|---|
| SECTIONS: | FLOWSHEET | ORDERS | ASSESSMENT | NCP | KARDEX | |
| FORMS: | ORDER SHEET | ORDER HISTORY | | | | |

| | 116 | STATUS | ORDER DATE / TIME | MD |
|---|---|---|---|---|
| | ORDER TEXT | | | |
| MEDS | DIGOXIN 0.125 mg IV qd | ACTIVE | 03/24 0900 | JB / LN |
| | MORPHINE SULFATE 1-5 mg IV q4h<br>PRN SEVERE PAIN | ACTIVE | 03/24 0900 | JB / LN |
| | AMPICILLIN 500 mg IVPB q6h | ACTIVE | 03/24 0900 | JB / LN |
| | VALIUM TABLET 5 mg ORAL qd  123 124<br>PRN RESTLESSNESS  122<br>121  125 | NOW | 03/24 0900 | JB / LN |
| IV'S | 500cc HS FLUSH SWAN-GANZ<br>1000 UNITS HEPARIN | ACTIVE | 03/24 0900 | JB / LN |
| | 250cc D5V LEFT ARM<br>50 mg NIPRIDA | ACTIVE | 03/24 0900 | JB / LN |
| | 500cc D5V TKO LEFT ARM | ACTIVE | 03/24 0900 | JB / LN |
| LAB | II & II | ACTIVE | 03/24 0900 | JB / LN |
| | LYTES | ACTIVE | 03/24 0900 | JB / LN |
| | EKG<br>HCL1 | ACTIVE | 03/24 0900 | JB / LN |

[NEW ORDER]       [SIGN]

| SECTIONS: | FLOWSHEET | ORDERS | ASSESSMENT | NCP | KARDEX | | | |
|---|---|---|---|---|---|---|---|---|
| FORMS: | ORDER SHEET | ORDER HISTORY | | | | | | |
| | ORDER TEXT | | | | STATUS | ORDER DATE / TIME | | MD |
| MEDS | DIGOXIN 0.125 mg IV qd | | | | ACTIVE | 03/24 | 0900 | JB / LN |
| | MORPHINE SULFATE 1-5 mg IV q4h PRN SEVERE PAIN | | | | ACTIVE | 03/24 | 0900 | JB / LN |
| | AMPICILLIN 500 mg IVPB q6h | | | | ACTIVE | 03/24 | 0900 | JB / LN |
| | VALIUM TABLET 5 mg ORAL qd PRN RESTLESSNESS | | | | NOW | 03/24 | 0900 | JB / LN |
| IV'S | 500cc HS FLUSH SWAN- 1000 UNITS HEPARIN | | | | TIVE | 03/24 | 0900 | JB / LN |
| | 250cc D5V LEFT ARM 50 mg NIPRIDA | | | | TIVE | 03/24 | 0900 | JB / LN |
| | 500cc D5V TKO LEFT A | | | | TIVE | 03/24 | 0900 | JB / LN |
| LAB | II & II | | | | TIVE | 03/24 | 0900 | JB / LN |
| | LYTES | | | | TIVE | 03/24 | 0900 | JB / LN |
| | EKG HCL1 | | | | TIVE | 03/24 | 0900 | JB / LN |

Patient: DOE, JOHN K. H 08/19/40 01-56-16 9NB ALLERGIES: CODINE

MEDICATION ORDER ENTRY
ORDER DATE: 03/24 —322
ORDER TIME: 0900 —323
ORDERING MD: JB —324
DRUG NAME: AMPICILLIN —325
ROUTE: IVPB —326
DOSE: 1 gram —327
FREQUENCY: q6h —328
NUMBER OF DOSES: 40 —329
START DATE: 03/24 —330
START TIME: 0900 —331
COMMENTS: —332

NEW ORDER            SIGN

| SECTIONS: | | | | 102 | | DOE, JOHN K.<br>H 08/19/40 01-56-16 | | 9NB<br>ALLERGIES: CODINE | |
|---|---|---|---|---|---|---|---|---|---|
| | FLOWSHEET | ORDERS | ASSESSMENT | NCP | KARDEX | | | 103 | |
| FORMS: | MEDS | VITALS | I/O | VENTILATOR | LABS | | | | |

| START<br>STOP | MEDICATION<br>DOSE | ROUTE | FREQUENCY | SCHED<br>TIME | ACTUAL<br>TIME | DOSE | ROUTE/SITE | COMMENTS | INITIAL |
|---|---|---|---|---|---|---|---|---|---|
| 03/24 0900<br>04/12 0900 | DIGOXIN<br>0.125 mg | IV | qd | 0900 | 0900 | 0.125 mg | IV | | LA |
| 03/24 1200<br>03/26 0800 | MORPHINE SULFATE<br>1-5 mg<br>PRN SEVERE PAIN | IV | q4h | 1200<br>1600<br>2000 | 1200 | 4 mg | IV | FOR PAIN<br>WITH RELIEF | LA |
| 03/24 1200<br>03/26 0800 | AMPICILLIN<br>500 mg | IVPB | q6h | 1200<br>1800 | | | | | |
| 03/24 0900<br>04/02 0900 | VALIUM TABLET<br>5 mg<br>PRN RESTLESSNESS | ORAL | qd | 0900 | | | | | LA |

MEDICATION ORDER ENTRY — 301

ORDER DATE: 03/24 — 302
ORDER TIME: 0900 — 303
ORDERING MD: JB — 304
DRUG NAME: VALIUM TABLET — 305
ROUTE: ORAL — 306
DOSE: 5 mg — 307
FREQUENCY: qd — 308
NUMBER OF DOSES:
START DATE: 03/24 — 309
START TIME: 0900 — 310
COMMENTS: PRN RESTLESSNESS — 311

SIGN

| 453A | | 7/7 10:30 | 7/7 11:00 | 7/7 11:30 | 7/7 12:00 | 7/7 12:30 | 7/7 13:00 | | | |
|---|---|---|---|---|---|---|---|---|---|---|
| VITALS | HEART RATE | 453B 70 | 72 | 162* 453C | 154 | 156* | 92 | | | |
| | 454A BLOOD PRESSURE | 454B | 454C | | 454C | 454C | | | | |
| | RESPIRATION RATE | | | | | | | | | |
| LABS | 459B K+ | | | 459C | | | 459C | | | |
| | 460B Na | 460C | 460C | | | 460C | | | | |
| | 461B BUN | | | | | | | | | |
| | 462B CREAT | | | | | | | | | |

*FIG. 8*

| 453A | | 7/7 10:30 | 7/7 11:00 | 7/7 11:30 | 7/7 12:00 | 7/7 12:30 | 7/7 13:00 | | | | |
|---|---|---|---|---|---|---|---|---|---|---|---|
| VITALS | HEART RATE | 453B  70 | 72 | 162* | 154 | 156* | 92 | | | | |
| 454A | BLOOD PRESSURE | 454B | 454C | 453C | 454C | 454C | | | | | |
| | RESPIRATION RATE | | | | | | | | | | |
| LABS | 459B  K+ | | | 459C | | | 459C | | | | |
| | 460B  Na | 460C | 460C | | | 460C | | | | | |
| | 461B  BUN | | | | | | | | | | |
| | 462B  CREAT | | | | | | | | | | |

ANNOTATION:
1130 – A.FIG, UNCONTROLLED VENT. RESPONSE, MED WITH DIG 0.25
1230 – CONT. TO HAVE RAPID HB, VERAPIMIL 10mg BOLUS GIVEN

FIG. 9

SPREADSHEET CELL HAVING MULTIPLE DATA FIELDS

This application is a continuation of prior application Ser. No. 07/408,166, filed Sep. 15, 1989, now abandoned.

RELATED INVENTIONS

The present invention is related to the following inventions, all assigned to the assignee of the present invention:

System Control Structure of a Hospital Information System and Method of Using Same, having Ser. No. 116,614, and filed on Nov. 3, 1987;

Medical Information System With Automatic Updating of Task List In Response to Charting Interventions on Task List Window Into An Associated Form having Ser. No. 268,822, and filed on Nov. 7, 1987, now U.S. Pat. No. 5,077,666;

Clinical Task List with Charting onto Underlying Form and Automatic Updating of Task List, having Ser. No. 268,323, and filed on Nov. 7, 1987, now U.S. Pat. No. 5,072,383.

Method for Generating Patient-Specific Flowsheets by Adding/Deleting Parameters, having U.S. Pat. No. 4,878,175 issued on Oct. 31, 1989;

Forms Manager, having Ser. No. 540,382 and filed on Jul. 19, 1990, a continuation of Ser. No. 322,740, now abandoned;

A Method for Displaying Information from an Information Based Computer System, having Ser. No. 407,979 and filed on Sep. 15, 1989;

A Method for Displaying Information from an Information Based Computer System, having Ser. No. 407,836 and filed on Sep. 15, 1989;

Electronic Data Storage Interface, having Ser. No. 408,178 and filed on Sep. 15, 1989;

Method for Updating Data in a Database, having Ser. No. 408,167 and filed on Sep. 15, 1989;

Method for Storing a Transaction in a Distributed Database System, having Ser. No. 408,164 and filed on Sep. 15, 1989;

A Method of Forming a Spreadsheet Display, having Ser. No. 407,972 and filed on Sep. 15, 1989; and Data Storage Audit Trail, having Ser. No. 409,230 and filed on Sep. 15, 1989.

FIELD OF THE INVENTION

The present invention relates, in general, to the use of spreadsheets in a computing system and, more particularly, to the cells used to form the spreadsheet.

BACKGROUND OF THE INVENTION

The present invention relates to an automated records management system. Such an automatic system has utility, for example, in a hospital based patient record keeping system. Patient record keeping systems are used for maintaining a wide variety of separate, often interrelated, types of medical records concerning patients.

Hand written patient record keeping systems have evolved through many years of careful refinement and enhancement into systems which maintain a detailed manual record of medical information concerning each patient. To meet the needs of different hospital entities (such as doctors, nurses, pharmacy, accounting, laboratory, etc.) a manual record keeping system would require that one piece of information be entered into multiple records.

In a typical manual patient record keeping system a patient chart, usually in the form of a notebook, is maintained at the nursing station for each patient. The notebook is divided into a plurality of individual tabbed sections, such as Physicians Orders, Kardex, Nursing Care Plan, Nursing Assessment, and Laboratory.

Each of the above sections is further subdivided into a number of forms. The forms are those which are appropriate to the individual patient and/or such patient's physician. For example, within the Laboratory section there may appear forms for chemistry, hematology, blood gas, and microbiology.

In addition, a "flowsheet" chart is usually kept at the patient's bedside. On the "flowsheet" chart there are individual areas for medications records, vital signs, intake/output, laboratory results, and other categories which are dependent upon the patient's affliction, such as intravenous (IV) drips.

The flowsheets are often a type of spreadsheet arranged by a progression of time versus a particular parameter. Each of the time/parameter intersections form a cell.

A limitation of the manual record keeping systems is the fixed size of the cell. This fixed size can cause limitations on the amount of data that may be placed in the cell. Alternatively, the fixed size of a cell may be a waste of space if it is made large enough to cover any contingency.

In electronic spreadsheets, such as Lotus 1-2-3, produced by Lotus Development Corp., or Excel, produced by Microsoft Corp., the cell sizes are adjustable but may contain only one piece of data or information. In medical record keeping it is often necessary to display multiple pieces of data or information in a single cell.

In the medical field, one cell in a flowsheet may have a form or report associated with it which expands on the information in the cell. The information contained on the associated form or report may be divided into the general categories of mandatory, optional, notational, or other information. The mandatory information is information that must be present and is normally entered in the cell. Optional information is information that will be entered in the cell if present on the form. Notational information is not entered directly to the cell but may be indicated in the cell by a notation or indicator.

In addition, it is desirable, from a standpoint of efficiency, that the cells be self adjusting to fit the data or information that may be present on the form or record. If there is mandatory information present but no optional information, the cell may be made smaller by removing the space that would otherwise be used for the optional information.

Accordingly, it is an object of the present invention to provide a spreadsheet cell which overcomes the above deficiencies.

A further object of the present invention is to provide a spreadsheet cell which has multiple data fields for displaying more than one piece of data or information.

Another object of the present invention is to provide a spreadsheet cell which is self adjusting in physical form to provide for the display of multiple data fields.

These and other objects and advantages are achieved in accordance with a preferred embodiment of the invention described below.

SUMMARY OF THE INVENTION

A particular embodiment of the present invention consists of a spreadsheet comprised of a plurality of cells. Each cell is separately identified by one or more parameters which often act as row and/or column labels. In a health care environment, these parameters will generally be a medical parameter and/or a time parameter. The cells are dynamically configured so that the size may be changed depending on the information to be displayed. Each cell may be associated with a form which contains information. The forms are visual representations of attributes of object instances. The information on a form is generally broken down into mandatory, optional, notational, and other information. Each cell will display the mandatory information and may display the optional information if present on the form. In addition, a notation (or indicator) will be displayed in the cell if notational information is present in the form.

BRIEF DESCRIPTION OF THE DRAWINGS

FIG. 2 is an information screen representing an ORDER SHEET form in an ORDERS section of a patient record;

FIG. 5 is a form of a cell of the information screen of FIG. 2;

FIG. 6 is a form of a second cell of the information screen of FIG. 2;

FIG. 7 is an information screen representing a MEDS form in a FLOWSHEET section of the patient record;

FIGS. 8 and 9 are two views of an information screen illustrating the notational feature of the present invention;

DETAILED DESCRIPTION OF THE DRAWINGS

Figure 1:
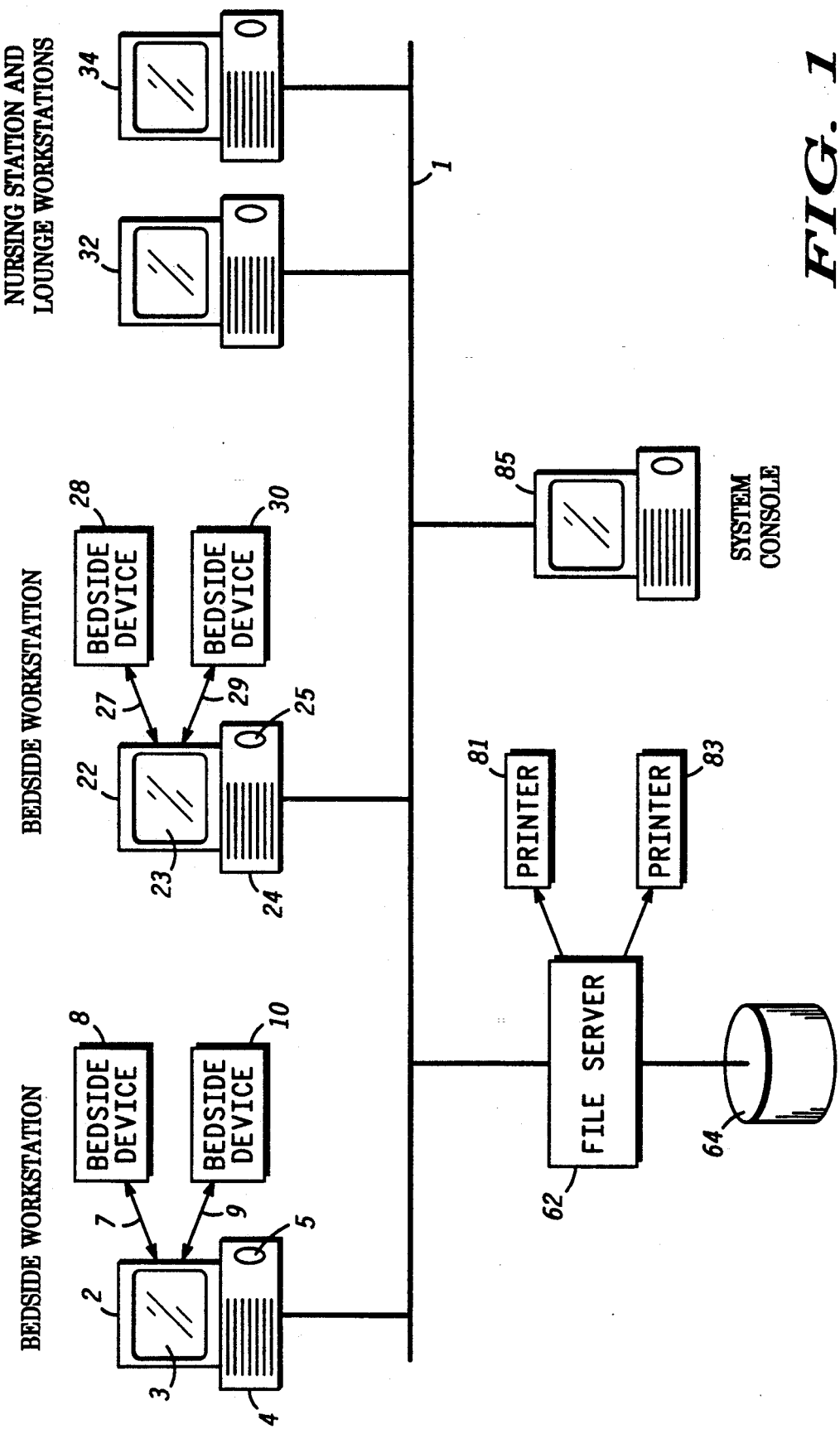
FIG. 1 is a block diagram illustrating a data processing system incorporating the present invention.

Referring initially to the block diagram of FIG. 1, a data processing system is illustrated. FIG. 1 shows a distributed computer system comprising a plurality of workstations 2, 22, 32, 34, and 85 coupled to a local area network (LAN) 1.

The system is typically installed for use in a nursing care unit, such as an intensive care unit, in a hospital or clinic. Terminals 2 and 22 are located at the patient bedside. One terminal may be dedicated to the use of a single patient, or it may be used for multiple patients. Terminals 32 and 34 may be located at a nursing station or nurse/physician lounge area. Terminal 85 is the system console which is used by a system administrator to configure and maintain the system and to provide additional services, such as displaying system status and error messages, archiving, and performing diagnostics.

Each bedside workstation or terminal, such as terminal 2, includes a video display unit with a viewable screen 3 for displaying information to the viewer; a housing 4 containing computing, data storage, and communications equipment and having associated with it a keyboard and pointing device such as a mouse 5; and connections 7 and 9 to one or more bedside devices 8 and 10. Bedside devices 8, 10, 28, and 30 may take the form of patient monitoring equipment suitable for the patient undergoing care, such as an EKG monitor, respiratory monitor, etc. Bedside terminal 22 may be coupled to a different set of bedside devices than those coupled to terminal 2.

The nursing station or lounge terminals 32 and 34, and system 85, may be identical to those used in the patient care unit but without the bedside device connections, or they may comprise slightly different equipment (e.g. personal computers) so long as they provide similar functionality.

Also coupled to LAN 1 is a file server 62 and associated storage device, here a disc storage device 64. File server 62 provides controlled access by workstations 2, 22, 32, 34, and 85 to write information to and to read information from disc storage device 64.

Optionally interfaces (not shown) may be used to couple various peripherals to LAN 1. For example, remote access modems may be coupled to one of such interfaces to provide access to the system from remote terminals (not shown) located elsewhere in the hospital or located off-site, such as at a physician's office or residence. Remote access may also be employed to diagnose system problems from an off-site facility. A laboratory system may be connected to an interface to permit the communication of laboratory information between the laboratory system and the clinical management system. An order communication system may be coupled to an interface to permit orders to be communicated from the system to other hospital systems (e.g. pharmacy or laboratory) and vice versa. An archival storage device may be coupled to an interface to permit any information stored in the system to be archived on suitable media, such as magnetic tapes or optical discs.

Printers 81 and 83 are coupled to file server 62 to allow patient information to be printed for the convenience of hospital personnel and to maintain a suitable legal record of all observations, orders, parameter readings, care plans, and other pertinent information regarding the monitored patients. Printers 81 and 83 may be any suitable printers such as, for example, laser printers or high speed dot matrix printers. A printer may optionally be coupled to the bedside terminal and/or the terminal at the nursing station or lounge, if desired.

In operation, the system user, typically a nurse or physician, conducts a dialog with the system through the use of a keyboard, mouse, light-pen, touch-pad, trackball, or other appropriate means for entering information. "Icons", screen-sensitive areas, or the equivalent, or any combination thereof which is appropriate to the end application, may also be provided.

The user provides information to or queries the system by means of the keyboard and/or pointing device, and receives information from the system by means of information displayed on the screen and/or through audible signals which could include speech synthesis.

Referring now to FIG. 2, an information screen, generally designated 100, is illustrated. Information screen 100 is an ORDER SHEET form from the ORDERS section of a patient record. Screen 100 generally consists of a patient demographics area 101, a message area 102, a sections area 103, a forms area 104, a display area 105, and a softkey area 106.

In the order sheet displayed in area 105, columns 110-113 are column parameters provided for the order text, status of the order, order date/time, and the doctor placing the order, respectively. The blocks below column headings 110-113 are data cells.

Figure 3:
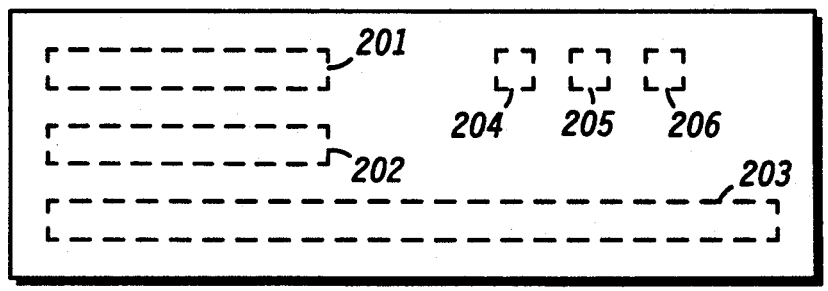
FIG. 3 is a cell of a screen, such as the information screen of FIG. 2, embodying the present invention.

A basic data cell, generally designated 200, is illustrated in FIG. 3. Cell 200 has several designated fields within the cell for displaying information. There are three basic types of information fields in cell 200: mandatory information fields designated by dashed lines 201 and 202; optional information fields designated by dashed line 203; and notational information fields designated by dashed lines 204-206.

Figure 4:
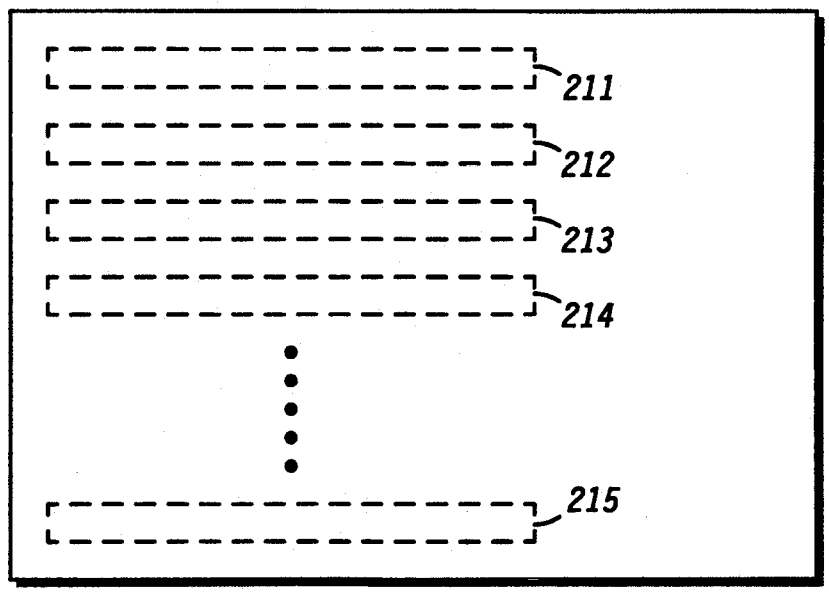
FIG. 4 is a form associated with a cell embodying the present invention.

In FIG. 4, a form, generally designated 210, is illustrated. Form 210 contains various information fields 211-215. Form 210 is a visual representation of attributes of object instances. Fields 211-215 contain information taken from various database records.

As shown in cell 120 of FIG. 2, there are several data fields 121-125. As will be explained below, fields 121-124 are mandatory information fields and field 125 is an optional information field. By selecting cell 120, the form, generally designated 300, associated with cell 120 may be displayed, FIG. 5. Form 300 contains a label field 301 and various information fields 302-311.

The information for mandatory field 121 of cell 120 is taken from field 305 of form 300. Likewise, the information for mandatory fields 122, 123, and 124 of cell 120 is obtained from fields 307, 306, and 308, respectively, of form 300. The information for optional field 125 of cell 120 is taken from field 311 of form 300.

It should be noted that the fields of form 300 are not divided into mandatory, optional, or notational fields. These designations are determined from the definitions of the cell when the cell is displayed.

Figure 5:
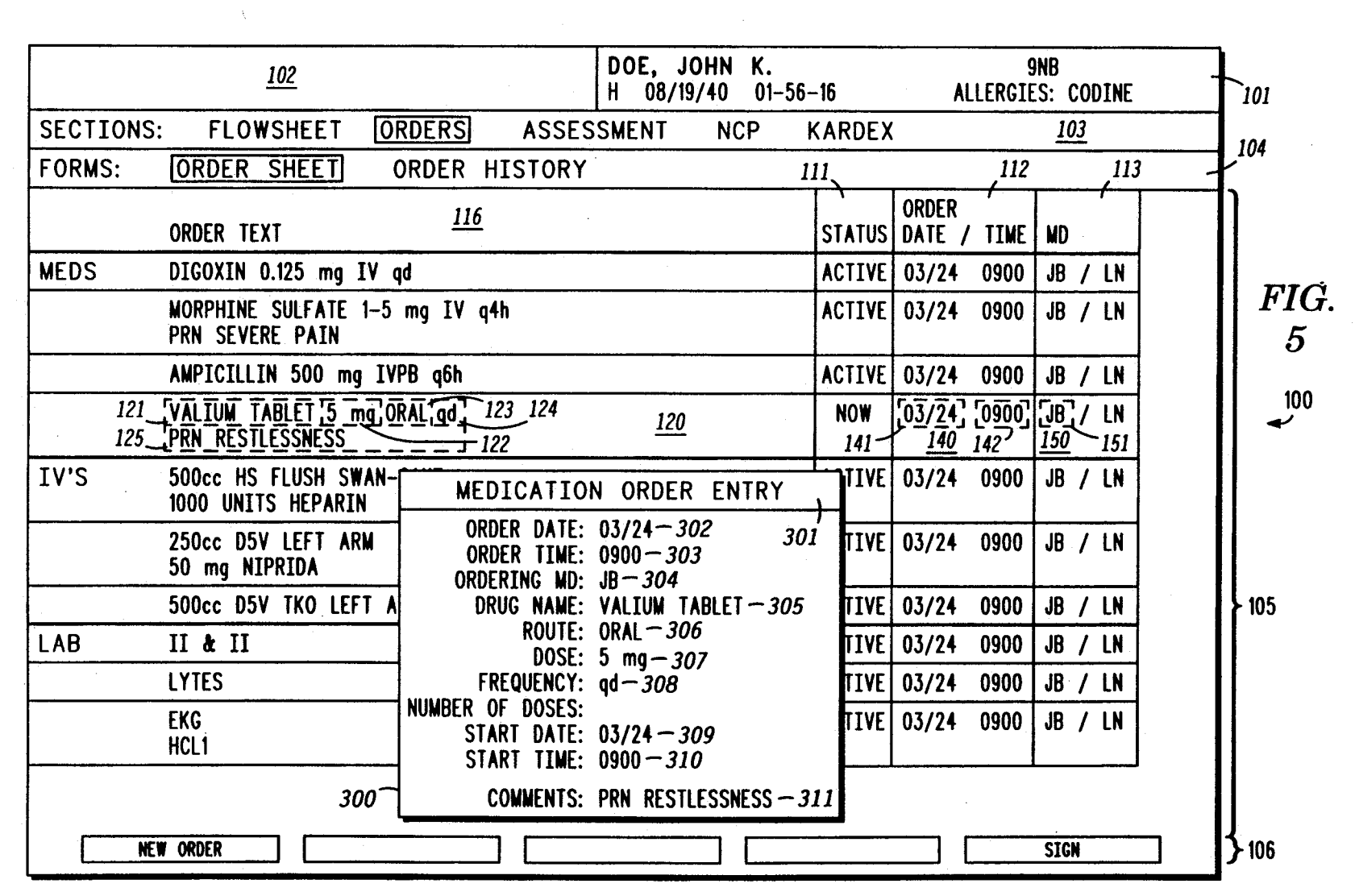

An example of how mandatory, optional, notational, or other information is displayed in a cell is illustrated in cells 140 and 150 of FIG. 5. Cell 140 has two mandatory fields 141 and 142. The order date taken from field 302 of form 300 is displayed in field 141. The order time taken from field 303 of form 300 is displayed in field 142.

Cell 150 has a mandatory field 151 used to designate the ordering doctor. This information is obtained from field 304 of form 300.

In addition to different types of cells containing different types of information, the same types of cells may contain different information. This is shown by comparing cell 120 of FIG. 5 to cell 130 of FIG. 6. Cell 130 contains mandatory fields 131-134 which correspond to mandatory fields 121-124 of cell 120. However, there is no field in cell 130 which corresponds to field 125 of cell 120. The reason for this is found in viewing form 320, the form for cell 130.

As shown in form 320, the comment field, field 332, is empty. Therefore, there is nothing to display in an optional field of cell 130 that would be equivalent to that displayed in optional field 125 of cell 120.

Because comment field 332 of form 320 is empty, the size of cell 130 is adjusted by reducing its height. This provides a more economical display.

Referring now to FIG. 7, a MEDS form from the FLOWSHEET section of a patient record is displayed in area 105 of information screen 100. This form has a cell 120' which is the equivalent of cell 120 of FIG. 2. In FIG. 7, the mandatory fields 121'-124' are displayed in different fields of cell 120' than mandatory fields 121-124 of cell 120. This shows the flexibility with which cells may be designed.

A cell has fields defined within its boundary. Each field may be associated with an attribute of an object instance associated with the cell. These fields may also be designated as mandatory, optional, or notational.

An example of a notational field is illustrated in FIG. 8. A sample form, generally designated 450, is illustrated in FIG. 8. Form 450 illustrates two groups of tiles, a vitals group 451 and a labs group 452. Vitals group 451 contains four tiles: a heart rate tile 453, a blood pressure tile 454, and a respiration rate tile 456. The labs group consists of: a K+ (Potassium) tile 459, a Na (Sodium) tile 460, a BUN (Blood Urea Nitrogen) tile 461, and a CREAT (CREATinine) tile 462.

Each tile 453-462 comprises several cells. For example, heart rate tile 453 has a group cell 453A and a title cell 453B. In a group, such as group 451, the name of the group may or may not be printed. Generally, only the first tile in the group, here tile 453, will designate the group name. Cell 453B contains the title, here the title is "Heart Rate". The remaining cells, such as in tile 454 are data cells 454C. One cell 454C is provided for every time period listed on the display. Cells 454C are spreadsheet type cells in that they repeat with time whereas cells 454A and 454B are non-spreadsheet cells that do not repeat with time. In tile 454, the group cell 454A is left blank since the group is displayed previously. However, the parameter cell 454B of tile 454 is labeled Blood Pressure. The data cells 454C of tile 454 are then aligned with the time intervals. This is described in more detail in the copending patent application "Forms Manager".

To illustrate the notational feature of the present invention, heart rate tile 453 will be utilized. Data has been entered for each time period in the corresponding cells 453C. In the 11:30 and 12:30 time periods, the cells also contain an asterisk (*). By selecting the cell, the information represented by the asterisk will be displayed in a form such as those shown in FIGS. 5-7. By selecting tile 453, all of the annotations for the tile will be displayed. This is illustrated in FIG. 9.

FIG. 9 contains a pop up window 470 which shows the annotations for the two time periods with the asterisks. The annotation for the 11:30 cell being "A. FIB, UNCONTROLLED VENT. RESPONSE, MED WITH DIG 0.25" and the annotation for 12:30 being "CONT. TO HAVE RAPID HR, VERAPIMIL 10 mg BOLUS GIVEN".

While the indicator shown here was a simple asterisk, there are generally three basic types of indicators: an annotation indicator used to indicate that a notation has been made to a value displayed in the cell; a correction/change indicator to show that a correction/change has been made to a value displayed in the cell; and an error indicator to show that some value displayed in the cell is in error (such as a temperature of 986°).

Rather than using an asterisk to indicated a notational field is present, as in FIGS. 8 and 9, other forms of indicators may be used. For example: different letters; color (by changing the background color of a cell where data has been corrected or changed); blinking text could be used to indicate that a value is outside a particular range; bold, inverse, or italic text; or any combination of the above may be used as indicators.

The cell sizes may be adjusted depending upon whether any of the foregoing notations are to be displayed within a cell. This is accomplished in the same manner as for optional fields described above.

Figure 10:
FIG. 10 is a view of an information screen illustrating a form associated with a parameter cell.

It should be noted that parameter cells are handled in the same manner as data cells. An example of this is illustrated in form 450 of FIG. 10. A DRIPS group 469 has been added which contains a tile 463 for a Dobutamine drip. By selecting cell 463B and activating the show detail option, a window of a form 470 is provided which contains the details of the Dobutamine parameter. As shown, the data of a medication field 471 of form 470 is placed in a field 481 of cell 463B; the data of an initial dose field 472 is placed in a field 483; and the data of an initial rate field 473 is placed in a field 482.

Figure 11:
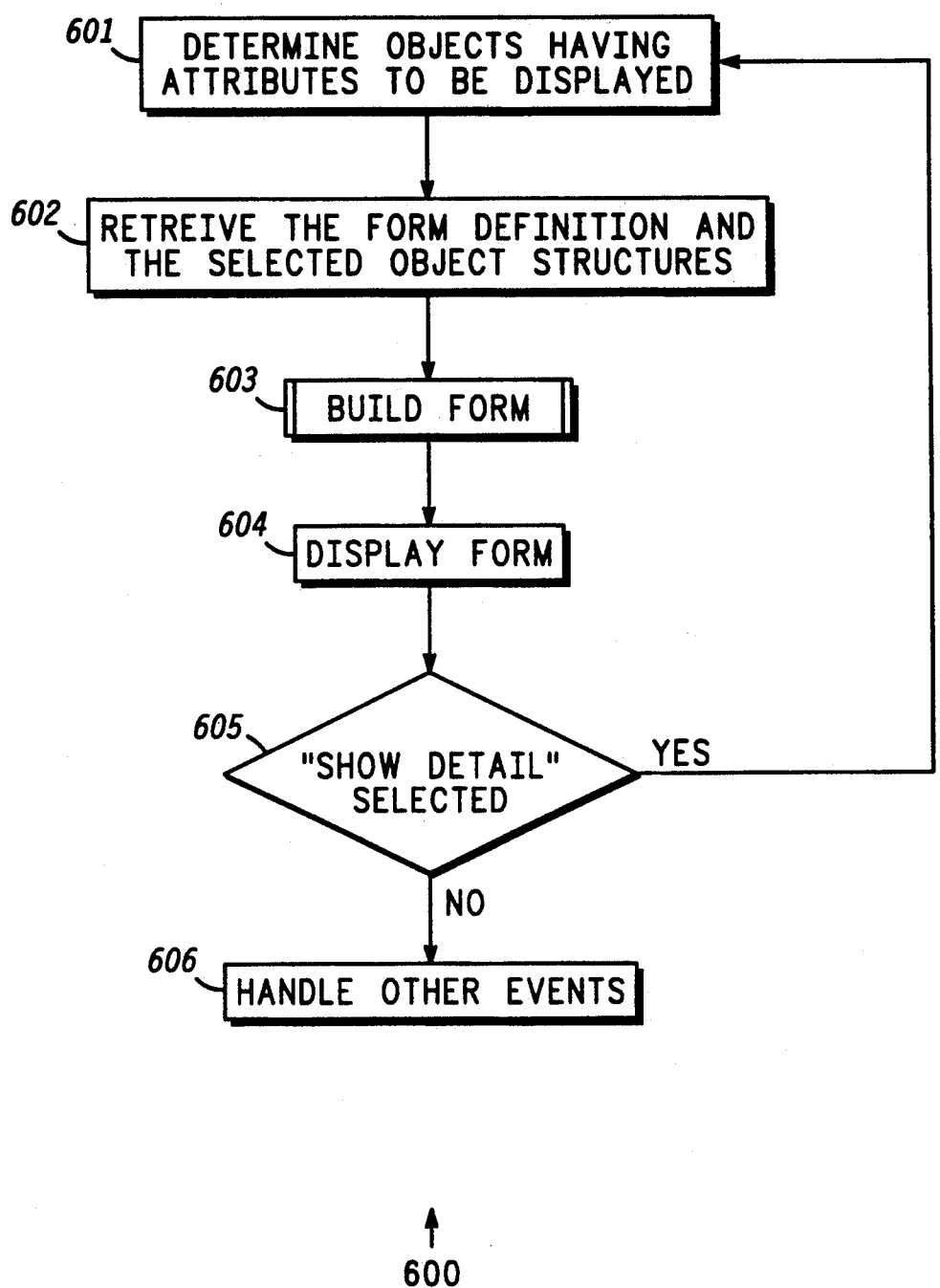
FIGS. 11, 12A and 12B are graphical representations of a process embodying the present invention.
Figure 12A:
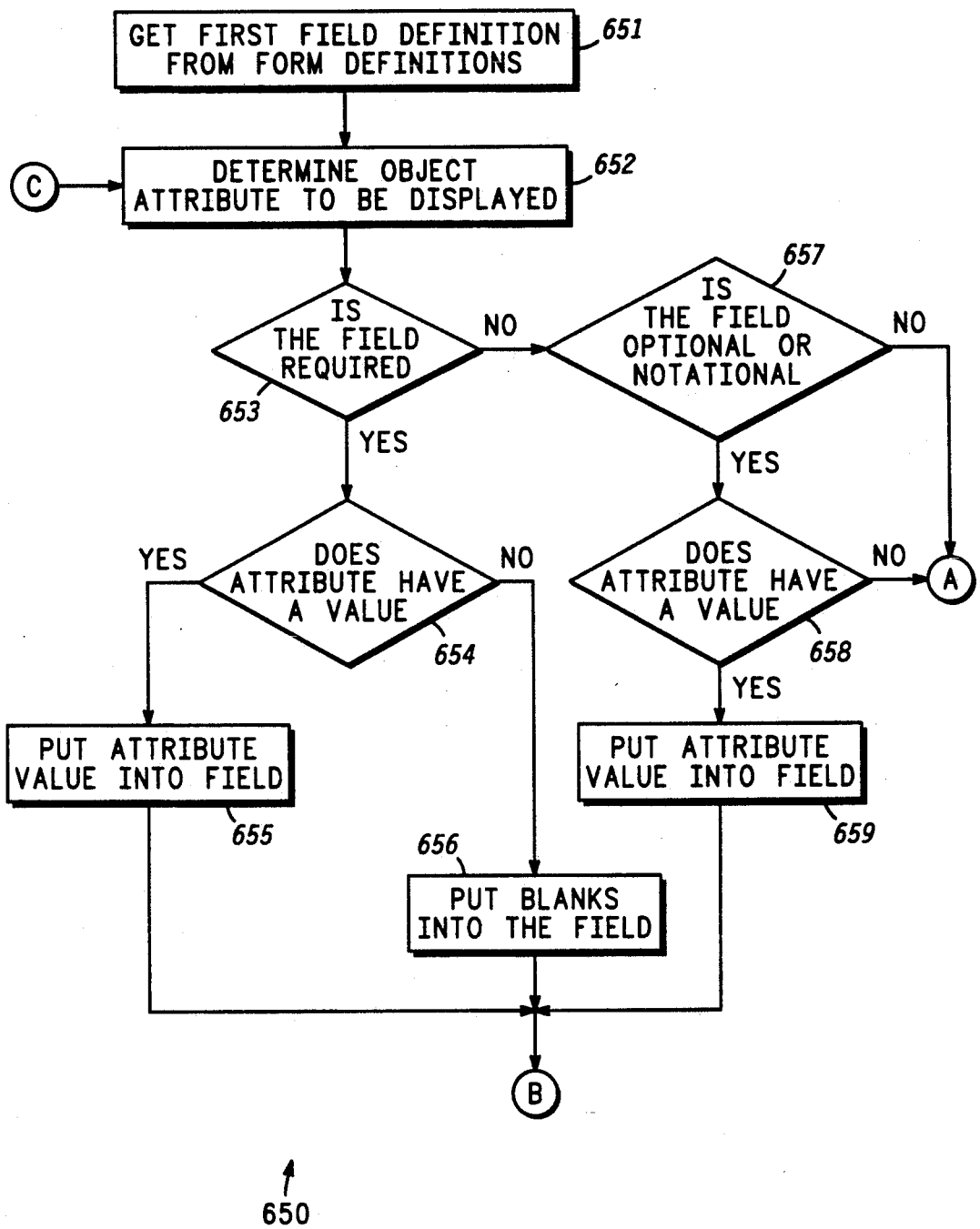
Figure 12B:
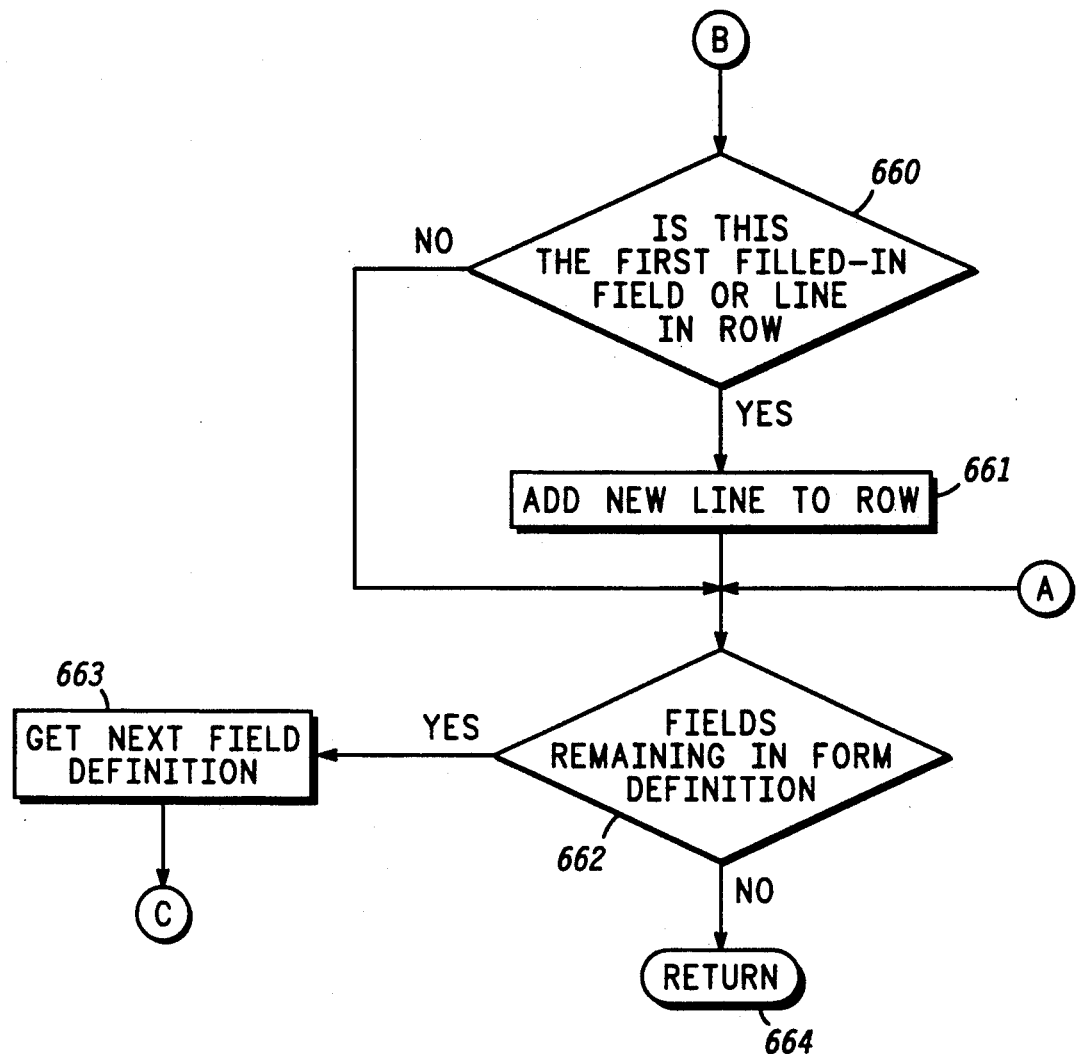

Referring now to FIGS. 11, 12A, and 12B, graphical representations of flow charts embodying the present invention are illustrated. The flow chart of FIG. 11, generally designated 600, illustrates the "Show Detail" option of the present invention. A copy of pseudo code for this process is illustrated in Appendix A.

The process is a continual loop which executes upon the occurrence of the "Show Detail" option being selected. The process commences with determining which objects have attributes to be displayed, step 601. Next, in step 602, the form definition for the form to be displayed and object definitions of the kinds of objects to be displayed are retrieved.

Once the form and object structures are identified, the form is built, step 603. This is described in more detail in FIGS. 12A and 12B. Once built, the form is displayed, step 604.

After the form is displayed, the process checks to see if another "Show Detail" option has been selected, decision step 605. If a "Show Detail" option has not been selected, the process moves on to handle other events, step 606. If the "Show Detail" option has been selected, the process loops back to step 601.

In FIGS. 12A and 12B, a flow chart, generally designated 650, detailing build form step 603 of FIG. 11 is illustrated. A copy of pseudo code for this process is illustrated in Appendix B. This process commences by obtaining the first field definition from the form definition, step 651. Next, in step 652, the attributes of the object instance to be displayed are determined.

In a decision step 653, the process then determines if the field is required to be displayed. If the field is required to be displayed, the process moves to decision step 654 and determines if the attribute has a value. If the attribute does have a value, the value is put into the field, step 655. If the attribute does not have a value, blanks are put into the field, step 656.

If the field is not required, step 653, the process moves to decision step 657 and determines if the field is optional or notational. If the field is optional or notational, the process moves to decision step 658 and determines if the attribute has a value. If the attribute does have a value, it is put into the field 659.

Following steps 655, 656, or 659, the process moves to decision block 660 and determines if this is the first filled-in field or line in the row. If this is the first filled-in field or line, a new line is added, step 661.

Following step 661, or if this is not the first filled-in field or line (step 660); if the field is not optional or notational (step 657); or if the optional or notational field does not have a value, the process moves to decision step 662. In step 662, the process determines if there are fields remaining in the form definition. If there are fields remaining, the next field is read and the process loops back to step 652. If there are no more fields remaining, the process returns, step 664.

Therefore, an apparatus has been shown which accomplishes the objectives of providing a cell having multiple data fields. This invention further provides a cell whose physical dimensions may be adjusted to meet the requirements of the fields to be displayed.

Thus, it will be apparent to one skilled in the art that there has been provided in accordance with the invention, a data cell that fully satisfies the objects, aims, and advantages set forth above.

While the invention has been described in conjunction with specific embodiments thereof, it is evident that many alterations, modifications, and variations will be apparent to those skilled in the art in light of the foregoing description. Accordingly, it is intended to embrace all such alterations, modifications, and variations in the appended claims.

---

APPENDIX A
SHOW DETAIL

Loop, await event
    Case Event "Show Detail"
        Get a database row descriptor for the object
        instances that have attributes to be displayed
        on the form.
        Given the row descriptor and a form name,
        retrieve the form definition and object
        structures from the database.
        Use the form definition to determine which of
        the objects' attributes to display in which
        fields of the form.
        Build the form.
        Display the form.
End of loop.

---

APPENDIX B
BUILD FORM

For each field in the form definition do:
    Based on the form definition for the field, determine
    which attribute of which object instance to display in
    the field.
    If the field is required:
        If the attribute has a value:
            Put the value into the field.
        Else:
            Put blanks into the field.
        If the new field is the first field to be
        filled-in on a line:
            Add a line to the row.
    If the field is optional:
        If the attribute has a value:
            Put the value in the field.
        If the new field is the first field to be
        filled-in on a line:
            Add a line to the row.

---

We claim:

1. A computer system for displaying a spreadsheet, said spreadsheet comprising a plurality of display cells, each of said display cells comprising a plurality of mandatory and optional display fields, said computer system comprising:

storage means for storing spreadsheet information including optional information associated with a plurality of information fields from a plurality of forms;

designation means for designating said mandatory and optionally display fields for each of said display cells from said information fields of said forms;

retrieval means for retrieving said spreadsheet information from said storage means corresponding to said designated mandatory and optional display fields for each of said display cells; and display means for displaying said spreadsheet information corresponding to each of said mandatory and optional display fields for each of said display cells, for displaying said optional information in said corresponding display cell only if said optional information is stored in said storage means and for automatically reducing said corresponding display cell in size if said optional information is not stored in said storage means.

2. A computer system for displaying a spreadsheet, said spreadsheet comprising a plurality of display cells, each of said display cells comprising a plurality of mandatory and notational display fields, said computer system comprising:

storage means for storing spreadsheet information including rotational information associated with a plurality of information fields from a plurality of forms;

designation means for designating said mandatory and notational display fields for each of said display cells from said information fields of said forms;

retrieval means for retrieving said spreadsheet information from said storage means corresponding to said designated mandatory and notational display fields for each of said display cells; and display means for displaying said spreadsheet information corresponding to each of said mandatory and notational display fields for each of said display cells, for displaying said notational information in said corresponding display cell only when said notational information is selected to be displayed and for automatically adjusting said corresponding display cell in size if said notational information is designated to be displayed.

3. The computer system as recited in claim 2, wherein said display means includes means for displaying an indicator in said notational display field of said corresponding display cell.

4. A method executed by a computer system as part of a computer-implemented program for displaying a spreadsheet, said spreadsheet comprising a plurality of display cells, each of said cells comprising a plurality of mandatory and optional display fields, said method comprising the steps of:

(a) storing spreadsheet information including optional information in memory associated with a plurality of information fields from a plurality of forms;

(b) designating said mandatory and optional display fields for each of said display cells from said information fields of said forms;

(c) retrieving from said memory said information corresponding to said selected mandatory and optional display fields, respectively, for each of said display cells;

(d) displaying on a display device said spreadsheet information associated with each of said mandatory display fields for each of said display cells;

(e) displaying said optional information in each of said corresponding display cells if said optional information is stored in said memory; and (f) automatically reducing said display cell if said optional information is not stored in said memory.

* * * * *

UNITED STATES PATENT AND TRADEMARK OFFICE
CERTIFICATE OF CORRECTION

PATENT NO. : 5,247,611
DATED : September 21, 1993
INVENTOR(S) : Ronald Norden-Paul, Richard Shelton and John Brimm It is certified that error appears in the above-indentified patent and that said Letters Patent is hereby corrected as shown below:

In column 8, claim 1, line 64, please delete the word "optionally" and insert therefore --optional--.

In column 9, claim 2, line 18, please delete the word "rotational" and insert therefore --notational--.

Signed and Sealed this

Twenty-fourth Day of May, 1994

Attest:

BRUCE LEHMAN

*Attesting Officer*　　　　*Commissioner of Patents and Trademarks*